United States Patent [19]

Wright et al.

[11] Patent Number: 5,030,224
[45] Date of Patent: Jul. 9, 1991

[54] CORONARY ARTERY RETRACTION CLIP

[75] Inventors: John T. M. Wright, Conifer, Colo.; Daniel Loisance, Paris, France; Noel L. Mills, New Orleans, La.

[73] Assignee: Pioneering Technologies, Inc., Wheat Ridge, Colo.

[21] Appl. No.: 411,837

[22] Filed: Sep. 25, 1989

[51] Int. Cl.$^5$ ............................................. A61B 17/00
[52] U.S. Cl. ..................................... 606/151; 127/20; 606/213
[58] Field of Search ................... 606/151, 213; 128/20

[56] References Cited

U.S. PATENT DOCUMENTS

| 2,232,142 | 2/1941 | Schumann | 606/138 |
| 2,238,563 | 4/1941 | Jacques | 128/20 |

FOREIGN PATENT DOCUMENTS 269293 11/1934 Italy ........................................ 128/20

OTHER PUBLICATIONS

Codman & Shurtleffle Catalog Page.

Primary Examiner—Stephen C. Pellegrino
Assistant Examiner—Gary Jackson
Attorney, Agent, or Firm—Grant L. Hubbard

[57] ABSTRACT

A coronary artery retraction clip consisting of a single piece of stainless steel wire formed into a uniquely shaped spring, partially covered with a soft, polymer coating to provide a non-slip surface allowing the clip to be readily gripped with surgical forceps, or the gloved hand is disclosed.

2 Claims, 1 Drawing Sheet

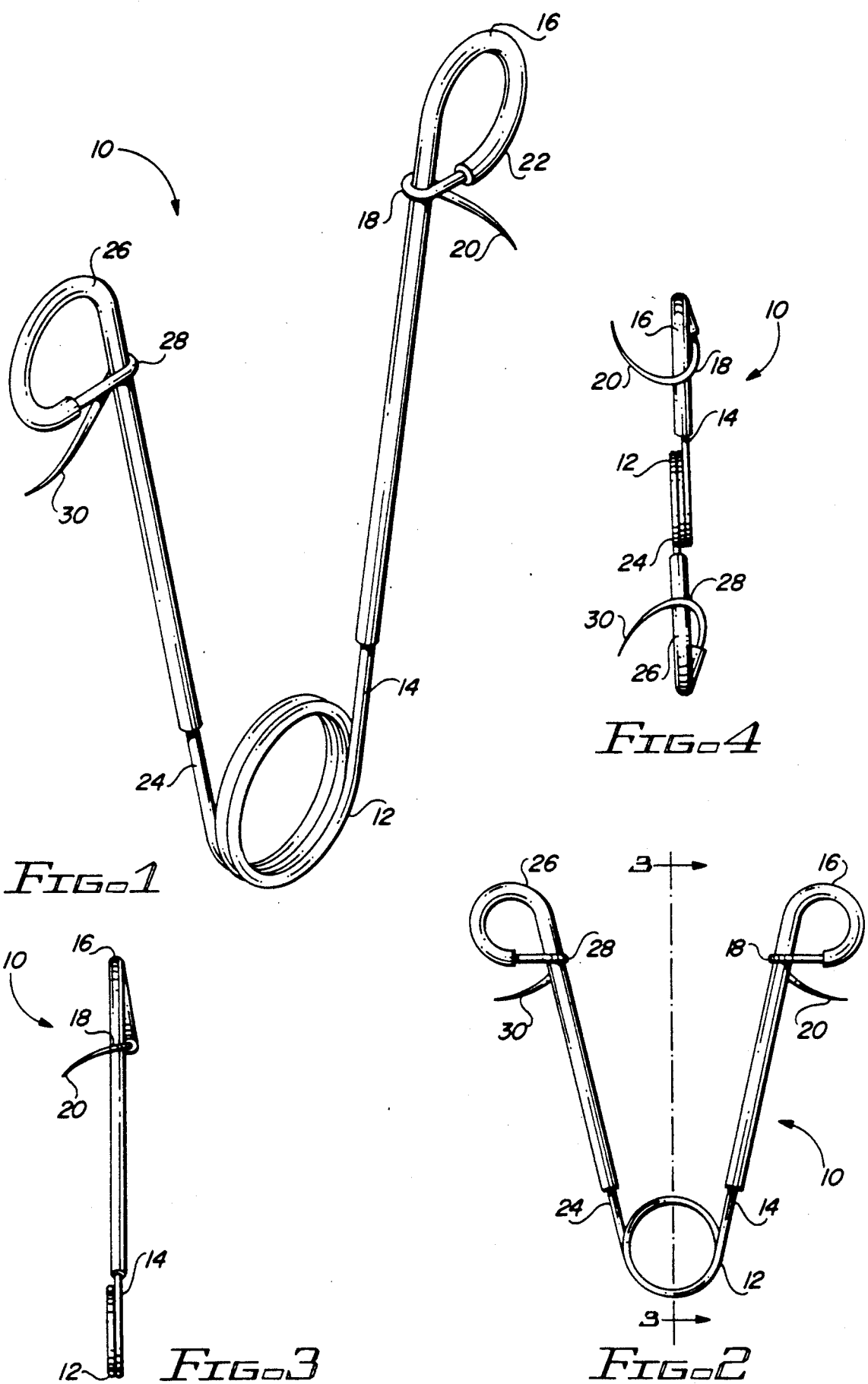

CORONARY ARTERY RETRACTION CLIP

BACKGROUND OF THE INVENTION

This invention relates to a single patient use disposable coronary artery retraction clip designed to improve exposure of the coronary artery during bypass surgery.

Intramuscular coronary anastomosis requires that the fat and tissue be retracted from the coronary artery to permit viewing and access to the coronary artery during surgery.

Epicardial retractors are known in the art. These devices, generally, are complex and expensive as well as being difficult to use. One exemplary retraction clip is manufactured by Codman & Shurtleffle, Randolph, Mass. 02368.

It is an object of this invention to provide an easily used, disposable coronary artery retraction clip which can be used with forceps and/or the surgeon's fingers to retract the fat and tissue away from the coronary artery.

SUMMARY OF THE INVENTION

The coronary artery retraction clip of this invention consists of a single piece of stainless steel wire formed into a uniquely shaped spring. The spring clip is partially covered with a soft, polymer coating to provide a non-slip surface allowing the clip to be readily gripped with surgical forceps, or the gloved hand.

In particularly, the present invention is a coronary artery retraction clip for retracting tissue from the coronary artery during coronary anastomosis formed of a length of biocompatible metal wire configured to form a central loop spring, first and second support arms extending from the loop spring diverging from each other and, at the proximal end of the respective first and second support arms, first and second eyes configured and constructed to receive forceps, and first and second hooks for engaging the tissue to be retracted, the central loop spring, support arms and eyes lying substantially in a single plane, the hooks extending out of said plain and outwardly from the respective arms, and preferably comprising first and second soft, resilient polymeric sleeves around wire which forms, respectively, the first and second arms and first and second eyes.

BRIEF DESCRIPTION OF THE DRAWINGS

FIG. 1 is a perspective view of the coronary artery retraction clip of this invention.

FIG. 2 is a side view of the access side of the coronary artery retraction clip of this invention.

FIG. 3 is view in partial cross-section of one half of the coronary artery retraction clip of this invention taken substantially along lines 3—3 in FIG. 2.

FIG. 4 is a view of the proximal end of the coronary artery retraction clip of this invention.

DESCRIPTION OF THE PREFERRED EMBODIMENT

The coronary artery retraction clip of this invention serves to temporarily retract open the fatty surface layer of the myocardium over the coronary artery to improve exposure of the vessel during coronary anastomosis.

The coronary artery retraction clip is described by means of somewhat arbitrary terms, e.g. access side, engaging side, proximal and distal ends, etc. with the understanding that these terms are used only to facilitate the description and are not related to the function or use of the coronary artery retraction clip.

The coronary artery retraction clip of this invention comprises a pair gripping eyes on the proximal end, from which a pair of engaging hooks extend toward the engaging side of the clip, one of the gripping eyes and one of the engaging hooks being resiliently biased away from the other of the eyes and hooks by a pair of arms connected to a spring at the distal end of the coronary artery retraction clip. The coronary artery retraction clip is symmetrical on two sides of the distal spring.

With reference now to the drawing, the coronary artery retraction clip 10 comprises a single or multiple loop spring 12 from which extends the two arms which, respectively, support the eyes and hooks. A first arm 14 extends to the right, as shown in FIG. 1 which views the coronary artery retraction clip from the access side, and is bent to form a first eye 16 and thence around the first arm 14, as indicated at 18, and extends outwardly from the arm and toward the engaging side to terminate in a first sharp pointed hook 20. A substantial portion of the arm and the eye comprise a polymeric sleeve.

The second arm 24 extends to the left, as shown in FIG. 1, and is essentially a mirror-image duplicate of the first arm. The distal end of the second arm 24 is bent to form a second eye 26 and thence around the second arm 24, as indicated at 28, and extends outwardly from the second arm and toward the engaging side to terminate in a second sharp pointed hook 30. A substantial portion of the second arm and the second eye comprise a polymeric sleeve.

The entire coronary artery retraction clip is formed of a single length of resilient stainless steel, or other biocompatible alloy metal, and two lengths of polymer tubing or polymer coating on the wire which forms the sleeve. Any biocompatible metal which has sufficient resiliency to form a spring may be used and any biocompatible polymer maybe used. Certain polymers, such as biocompatible polyurethane, which have a soft, resilient surface which is not slippery and thus permit more secure gripping are preferred, however. In the preferred embodiment, the spring 12 is formed of two or three loops of the wire lying side-by-side, but the number of loops may be varied. With some metals a single U-bend may be sufficient.

As seen in FIGS. 1 and 2, the first and second hooks extend in opposite directions from each other, i.e. outward from the center of the clip as viewed in FIG. 2, for example.

As seen in FIG. 3, and also in FIGS. 1 and 2, the first and second hooks also extend somewhat toward the distal end of the clip.

As seen in FIG. 4, the first and second hooks are curved first outwardly from the gripping side of the respective arms and then toward the plane in which the two arms lie.

The polymer sleeve permits the surgeon to grasp the coronary artery retraction clip securely with forceps or with his/her fingers, providing a soft resilient surface permitting secure gripping of the clip. The eyes formed of the central wire and polymer sleeve permit secure and easy gripping with forceps.

The general mode of use, which is described here, may be modified by surgeons to suit their individual techniques and preferences. The recommended directions for use are provided for completeness of disclosure.

The surgeon locates the artery and makes a suitable incision just through the fat layer over the vessel. The surgeon then chooses a retraction clip with appropriate prong lengths and compresses the clip, either by digital pressure, or by grasping the clip with suitable forceps, the tips of which may be passed through the non-slip, plastic covered loops. One of the sharp prongs of the clip should then be thrust gently into the fat layer on one side of the incision. The other prong is similarly pushed into the fat layer on the other side of the incision. Alternatively the prongs may be inserted into the fat layer one at a time, compressing the clip before the second is inserted. When the clip is slowly released the fat layer is retracted, exposing the coronary artery. The clip is easily removed by grasping each side in turn with forceps and gently pulling towards the anastomosis. To increase the spring force exerted by the clip the surgeon may use his fingers to apply sufficient digital outward force on the sides adjacent to the spring coils to cause permanent deflection. Support the coils while bending. Care must, of course, be taken to assure that the sharp prongs do not puncture the latex gloves.

The coronary artery retraction clip of this invention provides a simple, inexpensive and more easily used retraction clip than has heretofore been available.

INDUSTRIAL APPLICATION

The coronary artery retraction clip of this invention is useful in human and animal surgery.

What is claimed is:

1. A coronary artery retraction clip for retracting tissue from the coronary artery during coronary anastomosis comprising:
   a single, unitary length of biocompatible metal wire configured to form a central loop spring, first and second support arms extending from the loop spring diverging from each other and, at the proximal end of the respective first and second support arms, first and second eyes, and first and second hooks for engaging the tissue to be retracted, the central loop spring, support arms and eyes lying substantially in a single plane, the first and second eyes being formed of the metal wire lying substantially in said plane and configured to receive the tips of forceps substantially perpendicular to said plane, the hooks extending out of said plane and outwardly from the respective arms.

2. A coronary artery retraction clip for retracting tissue from the coronary artery during coronary anastomosis comprising:
   a length of biocompatible metal wire configured to form a central loop spring, first and second support arms extending from the loop spring diverging from each other and, at the proximal end of the respective first and second support arms, first and second eyes configured and constructed to receive forceps, and first and second hooks for engaging the tissue to be retracted, the central loop spring, support arms and eyes lying substantially in a single plane, the hooks extending out of said plane and outwardly from the respective arms and;
   first and second soft, resilient polymeric sleeves around wire which forms, respectively, the first and second arms and first and second eyes.

* * * * *